United States Patent [19]

O'Neill et al.

[11] Patent Number: 4,895,940

[45] Date of Patent: Jan. 23, 1990

[54] PROCESS FOR THE PREPARATION OF PENEMS

[75] Inventors: Brian T. O'Neill, Westbrook; Douglas Phillips, Ledyard, both, Conn.

[73] Assignee: Pfizer Inc., New York, N.Y.

[21] Appl. No.: 260,141

[22] Filed: Oct. 19, 1988

[51] Int. Cl.⁴ .................. C07D 499/04; A61K 31/425
[52] U.S. Cl. .................................. 540/310; 540/200; 514/192
[58] Field of Search ............... 540/200, 310; 514/195, 514/192, 193

[56] References Cited

U.S. PATENT DOCUMENTS

| | | | |
|---|---|---|---|
| 4,314,942 | 2/1982 | McCombie | 260/245.2 R |
| 4,443,373 | 4/1984 | Girijavallabhan et al. | 260/245.2 R |
| 4,443,463 | 4/1984 | McCombie | 424/270 |
| 4,530,793 | 7/1985 | Girijavallabhan et al. | 260/245.2 R |
| 4,584,133 | 4/1986 | Girijavallabhan et al. | 260/245.2 R |
| 4,610,823 | 9/1986 | DiNinno et al. | 540/350 |
| 4,614,737 | 9/1986 | Hamanaka | 514/193 |
| 4,614,738 | 9/1986 | Girijavallabhan et al. | 514/194 |
| 4,619,924 | 10/1986 | Hamanaka | 514/195 |
| 4,673,737 | 6/1987 | Evans et al. | 540/205 |
| 4,675,317 | 6/1987 | DiNinno | 514/192 |
| 4,690,922 | 9/1987 | Ganguly et al. | 514/210 |
| 4,739,047 | 4/1988 | Volkmann et al. | 540/310 |
| 4,751,297 | 6/1988 | Cue, Jr. et al. | 540/357 |
| 4,769,451 | 9/1988 | Dextraze | 540/350 |
| 4,782,145 | 11/1988 | Brighty et al. | 540/214 |

FOREIGN PATENT DOCUMENTS 257419  3/1988  European Pat. Off. .
54-66695  5/1979  Japan .

OTHER PUBLICATIONS

Andrus et al., *J. Am. Chem. Soc.*, 106, 1808–1811 (1984).
Afonso et al., *J. Am. Chem. Soc.*, 104, 6138–6139 (1982).
Barker et al., *Tet. Letters*, 28, 2283–2286 (1987).
DiNinno et al., *Tet. Letters*, 23, 3535–3538 (1982).
Ganguly et al., *J. Antimic. Chemoth.*, 9 (Suppl.), C1–C5 (1982).
Ghosez et al., *Tetrahedron*, 39, 2493–2503 (1983).
Girijavallabhan et al., *J. Antibiot.*, 39, 1182–1190 (1986).
Girijavallabhan et al., *Tet. Letters*, 24, 3179–3182 (1983).
Leanza et al., *Tetrahedron*, 39, 2505–2513 (1983).
Marchand-Brynaert et al., *Tet. Letters*, 21, 3085–3088 (1980).
Ona et al., *Chem. Pharm. Bull.*, 33, 4382–4394 (1985).

*Primary Examiner*—Nicholas S. Rizzo
*Attorney, Agent, or Firm*—Peter C. Richardson; J. Trevor Lumb; Robert K. Blackwood

[57] ABSTRACT

An efficient, multistep process for the synthesis of 6-(1-hydroxyethyl) 2-thio-substituted penem antibiotics from 2-[4R-(triphenylmethylthio)-3S-(1S-(dimethyl-t-butylsilyloxy)ethyl)-2-azetidon-1-yl]acetic acid esters.

28 Claims, No Drawings

PROCESS FOR THE PREPARATION OF PENEMS

BACKGROUND OF THE INVENTION

The present invention is directed to an efficient multistep process for the preparation of compounds of the formula (6), as shown in Scheme 3 below; and to certain of the intermediates, specified by the general formula (8) below, which find special value in this multistep process. The compounds of the formula (6) are useful as precursors of the various penem antibiotics specified by the formula (7), also shown in Scheme 3 below.

Heretofore, a number of processes have been reported for the preparation of penem antibiotics substituted at the 2-position with a thioether group, $-SR^2$, as found in the formulas (6) and (7) below. Two of the more general of these processes are illustrated in Schemes 1 and 2. In Scheme 1, an alternative intermediate to the silver salt of the mercaptan is the mercaptan itself, reportedly obtained by $Zn/H^+$ reduction of the tritylated thiol (Girijavallabhan et al., *J. Antibiotics* 39, 1182 (1986); U.S. Pat. No. 4,584,133).

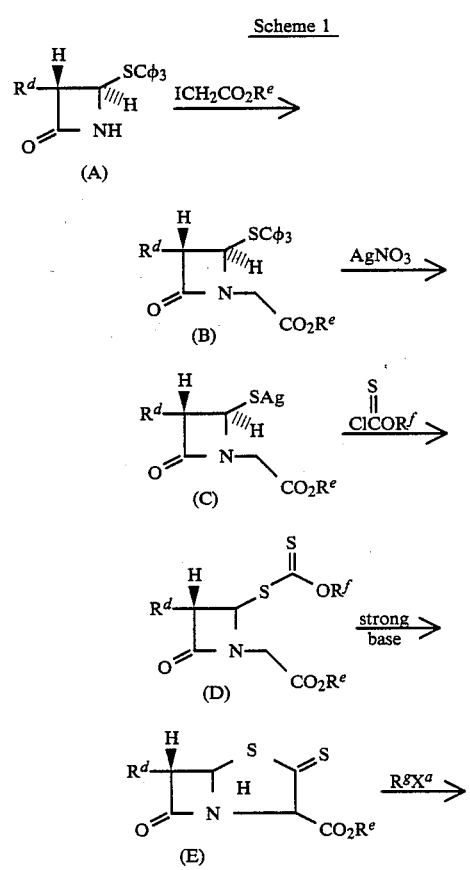

References:
Girijavallabhan et al., *J. Antibotics* 39, 1182 (1986); U.S. Pat. No. 4,584,133, wherein

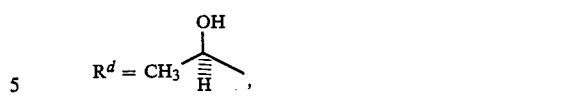

$R^e = -CH_2CH=CH_2$, $R^f$=beta-naphthyl, $R^g = C_2H_5$,

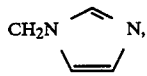

etc., $X^a$=leaving group.

DiNinno et al., U.S. Pat. No. 4,610,823 (1986); Leanza et al., *Tetrahedron* 39, 2505 (1983), wherein

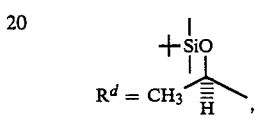

$R^e = -CH_2CH=CH_2$ or $-CH_2\phi NO_2$, $R^f = C_6H_5$, $R^g$=alkyl, aralkyl, etc., $Xk^a$=leaving group.

See also Girijavallabhan et al., U.S. Pat. Nos. 4,443,373 and 4,530,793 for an alternative synthesis of the components (E), wherein $R^d$ is $CH_3CHOH-$ and $R^e$ is $CH_2CH=CH_2$ or $CH_2CH_2OSi(CH_3)_3$, from the compound (A).

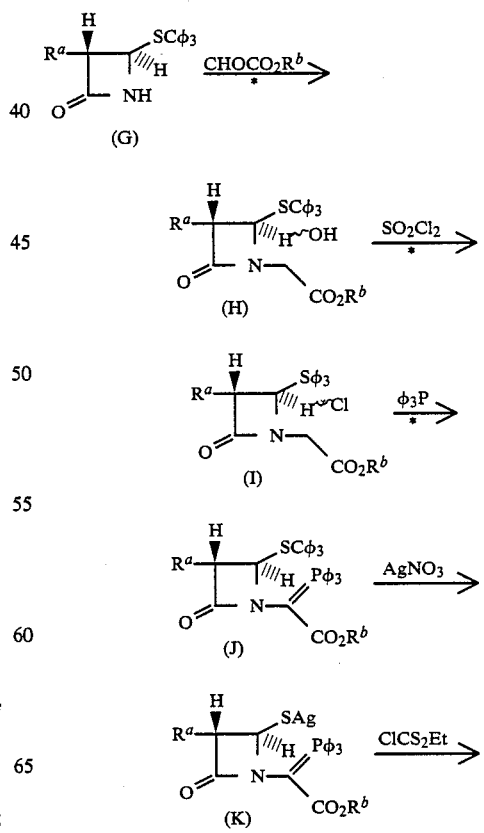

-continued
Scheme 2

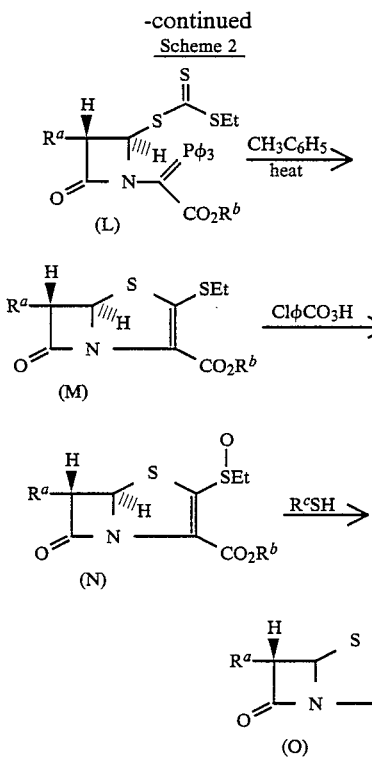

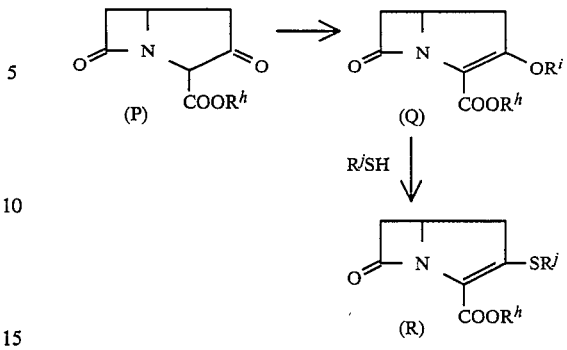

Reference
DiNinnio et al., *Tetrahedon Letters* 23, 3535 (1982), wherein:

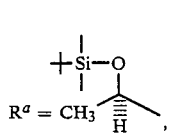

$R^b$ =—$CH_2CH$=$CH_2$, $R^c$ =—$CH(CH_3)_2$, —$CH_2C$-$H_2OH$, etc.

*These steps assumed on the basis of the footnote reference to U.K. 2,042,514.

See also Ganguly et al., *J. Antimicrob. Chemo.* 9, Suppl. Cl, (1982) using several similar steps in a different sequence.

Ghosez et al., *Tetrahedron Letters* 39, 2493 (1983) have described the synthesis of 2-oxopenams from penicillin G and the conversion of same to 2-alkoxypenem derivatives of penicillin G. Japanese Kokai 84-115,788 (Chem. Abst. 96:34979y, Derwent Abst. 78700D) similarly describes conversion of hydroxy and carboxy protected 6-(1-hydroxyethyl)-2-oxopenams to the corresponding alkoxy analogs.

Additional, alternative methods for the synthesis of penems include those described by Dextraze et al., U.S. Pat. No. 4,769,451; Pirie et al., U.S. Pat. No. 4,751,297; Volkmann et al., U.S. Pat. No. 4,739,047; Brighty, U.S. Pat. No. 4,695,626; and Brighty et al., U.S. Pat. No. 4,782,145.

There have been numerous reports in the literature concerning the conversion of 2-oxo-carbapenams and 3-oxocephams to 2-(alkylthio)-2-carbapenems and 3-alkylthio-3-cephems via enolic esters:

where $R^h$ is a conventional carboxy protecting group, $R^i$ is, for example, diphenyl- or diethylphosphoryl, tosyl, mesyl, or trifluoromethanesulfonyl. See for example Sletzinger et al., *Tetrahedron Letters* 21, 4221 (1980); Andrus et al., *J. Am. Chem. Soc.* 106, 1808 (1984); Evans et al., *Tetrahedron Letters* 26, 3787 (1985), and 27, 3119 (1986) and U.S. Pat. No. 4,073,737; Ratcliffe et al., 21, 31 (1980); ibid. 1979, 4947; Salzmann et al., ibid. 21, 1193 (1980); Melillo et al., ibid. 21, 2783 (1980); Iimori et al., and *J. Am. Chem. Soc.* 105, 1659 (1983). However, the chemistry observed with these carbapenem ketone groups has been generally inapplicable to the thiolactone carbonyl group of 2-oxopenems. For example, the reaction of mesyl chloride or mesyl anhydride with a compound of the type (4) below produces a compound of the type

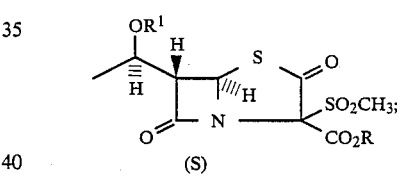

while either tosyl chloride or triflyl chloride and a compound of the type (4) produces a compound of the type:

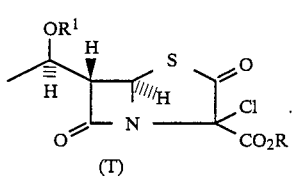

More recently it was specifically reported in published European patent application No. 257,419 that a compound of the type (4) below was reacted with diphenylphosphoryl chloride to form the diphenylphosphoryl ester in situ, which was in turn reacted with a phenol to form a compound of the type

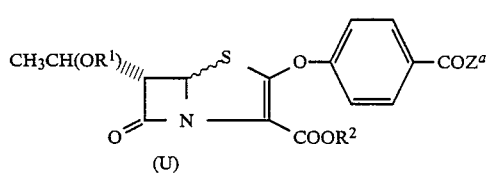

in very low yield. This application offers no specific support for the asserted broader use of other potential enol ester forming reagents such as triflyl chloride, which is in fact a known chlorinating agent, *not* a triflate ester forming reagent (vide supra; and Hakimelahi et al., *Tetrahedron Letters*, 1979, pp. 3643-3644).

SUMMARY OF THE INVENTION

We have now discovered an efficient multistep process for the synthesis of penem antibiotics, as summarized in Scheme 3. In particular, the present invention is directed to the processes of combined chemical steps:

(1) →(2) →(3) →(4);

(1) →(2) →(3) →(4) →(5) →(6); and (4) →(5) →(6).

In Scheme 3, the various variable symbols are defined as follows:

R is —CH$_2$CX=CH$_2$, —CH$_2$CH$_2$Si(CH$_3$)$_3$
p-nitrobenzyl, or a conventional radical forming an ester which is hydrolyzed under physiological conditions;
X is H or Cl; and
R$^1$ is a conventional silyl protecting group; and
R$^2$ is a pharmaceutically acceptable radical.

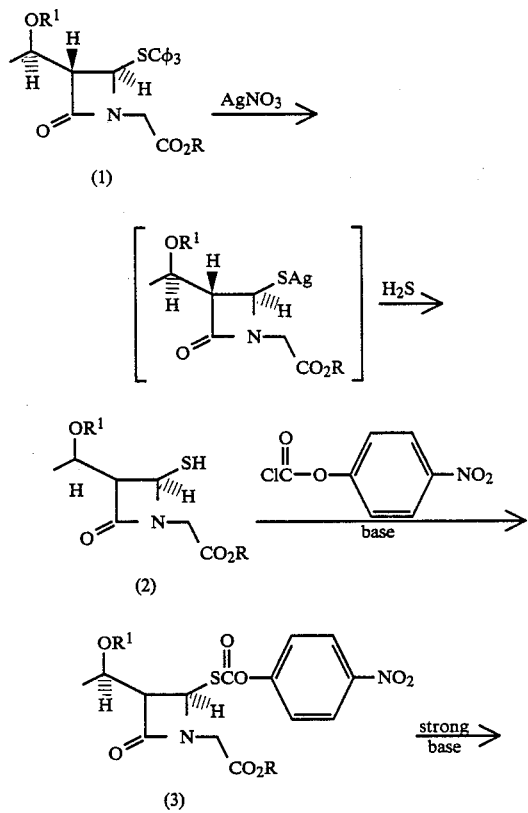

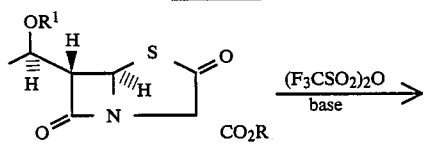

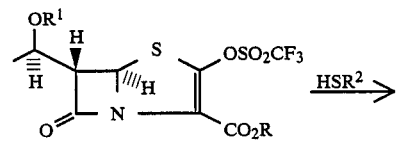

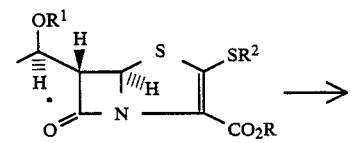

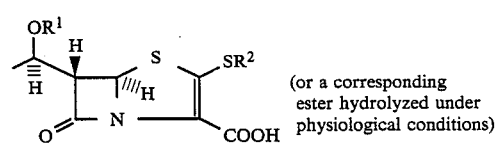

Conventional radicals which form esters which are hydrolyzed under physiological conditions have become as common in the beta-lactam art as pharmaceutically-acceptable salts. As in the case of numerous other beta-lactam antibiotics, such "pro-drug" esters are generally used orally to enhance gastrointestinal absorption. Once absorbed, they are hydrolyzed in vivo to form the corresponding penem acid. Preferred ester radicals are —CHR$^2$OCOR$^3$ or —CHR$^2$OCO$_2$R$^3$, where R$^2$ is hydrogen or methyl and R$^3$ is (C$_1$-C$_8$) alkyl, most particularly pivaloyloxymethyl and 1-(ethoxycarbonyloxy)ethyl.

Among the conventional silyl protecting groups are trimethylsilyl and dimethyl-t-butylsilyl. The latter is most preferred for its ease of introduction and removal, while at the same time possessing excellent stability as a protecting group during the various other process steps of the present invention.

Pharmaceutically acceptable radicals R$^2$ have been extensively defined in the prior art, as will be evident from the following prior art references:

(a) Hamanaka, U.S. Pat. No. 4,614,737;
(b) Girijavallabhan et al., U.S. Pat. No. 4,614,738;
(c) Hamanaka, U.S. Pat. No. 4,619,924;
(d) Girijavallabhan et al., U.S. Pat. No. 4,443,463;
(e) Girijavallabhan et al., U.S. Pat. No. 4,530,793;
(f) Girijavallabhan et al., U.S. Pat. No. 4,584,133;
(g) Ganguly et al., U.S. Pat. No. 4,690,922;
(h) McCombie, European published application No. 61,205;
(i) Hamanaka, European published application No. 132,101;
(j) Hamanaka, European published application No. 138,539;

(k) Perrone et al., European published application No. 199,490;

(l) Takemura et al., European published application No. 210,883;

(m) Kirkup et al., European published application No. 238,285;

(n) Sunegawa et al., European published application No. 243,686;

(o) McCombie et al., European published application No. 257,602; and (p) DiNinno et al., *Tetrahedron Letters* 3535 (1982).

Preferred values of $R^2$ found in the prior art (as noted by lower case letter from the list of references immediately above) are as follows:

($C_1$-$C_4$)alkyl (b, e, h, p), (1,3-dioxacyclopent-4-yl)methyl (a), (1,3-dioxacyclopent-2-yl)methyl (a), (2-oxo-1,3-dioxacyclopent-4-yl)methyl (a), (1-methyl-2-imidazolyl)methyl (i), piperidinomethyl (k), 2-hydroxyethyl (b, e, h), 2-(p-nitrobenzyloxycarbonylamino)ethyl (e, h), 2-(piperidino)ethyl (b), 2-(pyrrolidino)ethyl (b), 2-(morpholino)ethyl (b), 2-(4-(allyloxycarbonyl)piperazino)ethyl (b), 1-oxo-3-thiolanyl (cis and/or trans) (c), 1,1-dioxo-3-thiolanyl (c), 1-oxo-3-thianyl (cis and/or trans) (c), 1,1-dioxo-3-thianyl (c), 1-oxo-4-thianyl (cis and/or trans) (c), 1,1-dioxo-4-thianyl (c), 4-hydroxy-3-thiolanyl (m), 4-hydroxy-1-oxo-3thiolanyl (cis and/or trans) (m), 4-hydroxy-1,1-dioxo-3-thiolanyl (m), 4-hydroxy-3-furyl (m), 1,3-dioxacyclohex-5-yl (a), 2-oxo-1,3-dioxacyclohex-5-yl (a), 1-(p-nitrobenzyloxycarbonyl)-3-pyrrolidinyl (e, f), 2-oxo-3-pyrrolidinyl (j, o), 1-methyl-5-(dimethylaminocarbonyl)-3-pyrrolidinyl (n), 1-methyl-5-(2-(dimethylaminocarbonyl)ethyl-3-pyrrolidinyl (n), and trans-4-hydroxy-1-(benzyloxycarbonyl)-3-pyrrolidinyl (m).

The most highly preferred values of $R^2$ in the present process are $-C_2H_5$, $-CH_2CH(CH_3)_2$, $-CH_2CH_2OH$,

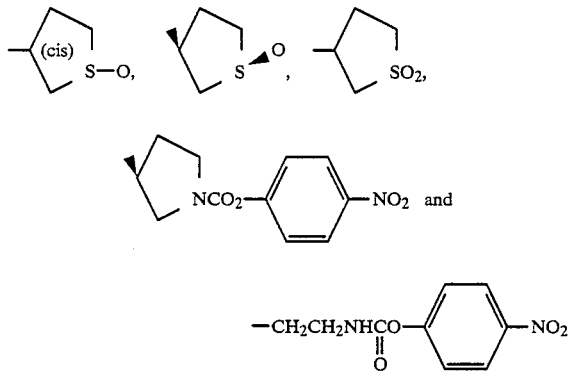

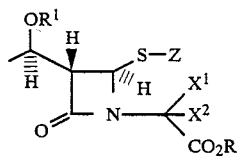

In addition to the processes noted above, the present invention is also specifically directed to novel intermediates of the formulas (3) and (5), shown in combined form by the formula

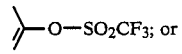

(8)

wherein R and $R^1$ are as defined above; and z, $X^1$ and $X^2$ are taken together and are $\rangle\!-\!O-SO_2CF_3$; or Z, $X^1$ and $X^2$ are taken separately, $X^1$ and $X^2$ are each hydrogen, and Z is p-nitrophenyloxycarbonyl.

DETAILED DESCRIPTION OF THE INVENTION

The present invention provides an efficient process for penem antibiotics having the formula (7) which is readily carried out.

In the first step of this process, a triphenylmethylthio compound of the formula (1), in the presence of two or more molar equivalents of a weakly basic amine such as pyridine and in the dark, is reacted with silver nitrate (at least one molar equivalent, usually in excess, e.g., 1.5-2 molar equivalents) to produce the silver salt of the corresponding mercaptan. This reaction is generally carried out in a reaction inert solvent, such as methanol. Temperature is not critical, but lower temperatures, e.g., $-25°$ to $25°$ C. are generally preferred, with $0°$-$5°$ C. particularly convenient and satisfactory. Generally without isolation the intermediate silver salt is converted directly with excess hydrogen sulfide gas to the mercaptan. Silver is recovered as the sulfide by filtration and the mercaptan (2) recovered from the mother liquor by conventional methods such as extraction and solvent evaporation.

As used herein, the expression "reaction inert solvent" refers to a solvent which does not interact with starting materials, reagents, intermediates or products in a manner which adversely affects the yield of the desired product.

In the second step, the mercaptan (2) is reacted with substantially one molar equivalent of 4-nitrophenyl chloroformate to form the intermediate compound of the formula (3). This step is carried out in the presence of substantially one molar equivalent of a tertiary amine, preferably diisopropylethylamine and/or dimethylaminopyridine, usually in a reaction inert solvent such As tetrahydrofuran, and is preferably carried out at lower temperatures, e.g., $-25°$ to $25°$ C., conveniently at $0°$-$5°$ C. If desired, the intermediate (3) is isolated and characterized by conventional methods. However, it is preferred to simply employ the initially obtained solution of the compound of formula (3) directly in the next step.

In the third step, the intermediate (3) is cyclized in the presence of a strong base to form the desired 2-oxopenem of the formula (4), a known compound, for example, when R is allyl. Preferably, this step is carried out on a solution of the compound of the formula (3) in a reaction inert solvent such as tetrahydrofuran. The preferred strong base is lithium hexamethyldisilylamide in the same reaction inert solvent, generally used in a large molar excess (e.g., 3-5 molar equivalents). This base, conveniently purchased as a 1M solution in tetrahydrofuran, is generally diluted (e.g., to about 0.1 to 0.2M) with tetrahydrofuran and cooled to low temperature (e.g., $-50°$ to $-100°$ C., conveniently $-78°$ C., the temperature of an acetone-dry ice bath. A solution of the compound of the formula (3) in the same solvent is added portionwise, maintaining the same low temperature. The reaction, which is substantially complete upon completion of the addition, is conveniently quenched with excess acetic acid and the 2-oxopenem (4) isolated by conventional methods of concentration and extraction.

In the next step the 2-oxopenem (4) is reacted with freshly distilled triflic anhydride, generally in slight molar excess, at reduced temperature (0° to −90° C., conveniently −78° C.) in a reaction inert solvent such as methylene chloride in the presence of a molar excess (generally 4–6 molar equivalents) of a tertiary amine, preferably diisopropyl ethyl amine. If desired, the resulting enolic triflate ester of the formula (5) is isolated by chromatography of the reaction mixture on silica gel and characterized. However, this is unnecessary, the reaction solution being well-suited for direct reaction with a mercaptan $R^2SH$ in the next step.

In the fifth step of the present sequence, in its preferred embodiment, a solution of the appropriate mercaptan, $R^2SH$, conveniently dissolved in the same reaction inert solvent such as methylene chloride, is added portionwise to the cold solution of the triflate ester (5), generally allowing the temperature to rise no more than about 10°–40° C. from its initial value, i.e., a temperature in the range of about 0° to −90° C. Upon completion of the reaction, the desired penem intermediate of the formula (6) is isolated by conventional methods, as exemplified below.

When R is a conventional radical forming an ester which is hydrolyzed under physiological conditions, and absent an amino protecting group in the radical $R^2$, the penem antibiotic is obtained by conventional removal of the silyl protecting group, e.g., by methods specifically exemplified below. When R is $-CH_2CX=CH_2$, $-CH_2CH_2Si(CH_3)_3$ or p-nitrobenzyl, an additional conventional chemical step is required to form the acidic penem antibiotic of the formula (8), or its pharmaceutically acceptable salt.

When R is $-CH_2CX=CH_2$, the group is best removed by the action of at least one molar equivalent of an alkali metal salt of an acid such as 2-ethylhexanoic acid in a reaction inert solvent such as ethyl acetate, in the presence of catalytic amounts of triphenylphosphine and tetrakis(triphenylphosphine)palladium, directly forming the alkali metal salt of the penem antibiotic. When $R^2$ contains nitrogen protected by an allyloxycarbonyl group, said group is removed by the same method.

When R is $-CH_2CH_2Si(CH_3)_3$, the group is best concurrently removed with the dimethyl-t-butylsilyl protecting group, preferably using a molar excess of tetrabutylammonium fluoride in a reaction inert solvent such as tetrahydrofuran.

When R is p-nitrobenzyl, the group is generally removed by conventional hydrogenolysis over a noble metal catalyst, preferably palladium, for example palladium-on-carbon. When $R^2$ contains a nitrogen protecting group such as benzyloxycarbonyl, said group is removed by the same method.

The mercaptans required for the present reaction sequence are generally known or available by conventional methods. A preferred method for the synthesis of 3S-mercaptothiolane 1R-oxide is specifically described below.

The penem antibiotics of the formula (7), as well as their pharmaceutically acceptable salts and esters, are employed in medicine according to methods described in references cited above.

It will be specifically noted that the compounds the of the formula (6) wherein $R^2$ is

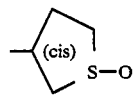

are used to prepare the corresponding product of Hamanaka, U.S. Pat. No. 4,619,924, i.e., the compound of the above formula (7), or an ester with $R^2$ of the same value. These products are a mixture of diastereoisomers, one having $R^2$ as 1R-oxo-3S-thiolanyl and the other $R^2$ as 1S-oxo-3R-thiolanyl. Of these, the 1R,3S-isomer of the formula

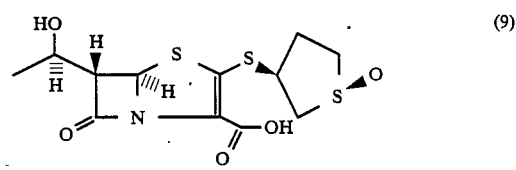

and its pharmaceutically acceptable salts and esters are preferred. This is not only because these compounds, and their several immediate precursors, are single, homogeneous compounds, such that the quality of the final products is much better controlled relative to the previously reported diastereomeric mixture (an important factor in clinical use), but because they show clinical advantages over Hamanaka's diastereomeric mixture.

The pure diasteromeric, antibacterial compound of the formula (9), its salts and its esters are tested, formulated and used according to methods detailed in above cited Hamanaka, U.S. Pat. No. 4,619,924, hereby incorporated by reference. Within the human dosage ranges there disclosed, the more preferred dosage range for these compounds is about 10–80 mg/kg/day, both orally and parenterally. These figures are illustrative only, since in some circumstances the attending physician will find it more beneficial to employ dosages outside of these ranges. In vivo hydrolyzable esters, particularly the pivaloyloxymethyl and 1-(ethoxycarbonyloxy)ethyl esters, are preferred in oral use, while the sodium or potassium salts are particularly preferred for parenteral use.

The following examples are given by way of illustration and are not to be construed as limitations of this invention, many variations of which are possible within the scope and spirit thereof.

EXAMPLE 1

Allyl 2-[4R-Mercapto-3S-(1S-(dimethyl-t-butyl silyloxy)ethyl)-2-azetidinon-1-yl]acetate A solution of 20 g (33.2 mmol) of allyl 2-[4R-(triphenylmethylthio)-3S-(1S-(dimethyl-t-butylsilyloxy)-ethyl)-2-azetidinon-1-yl]acetate (Jeff et al., Tetrahedron, vol. 39, 2505–2513, 1983; U.S. Pat. No. 4,610,823) in 600 ml of methanol was cooled to 0° C. and was treated with 5.94 ml (73 mmol) of pyridine. The following portion of the reaction sequence was conducted with the reaction flask protected from light. To the solution was added solid silver nitrate (10.2 g, 60 mmol) and the reaction mixture was allowed to stir for 1.5 hours while maintained at 0° C. Once this reaction was complete, hydrogen sulfide gas was slowly introduced with constant stirring. The dark mixture was then filtered through celite with recovery of silver sulfide and the filtrate was concentrated. The organic residue was partitioned between ethyl acetate and brine. The layers were separated and the aqueous phase was reextracted with fresh ethyl acetate. The combined organic layers were dried over sodium sulfate and were then evaporated to yield title product which was used directly in the next step.

EXAMPLE 2

Allyl 2-[4R-=(4-Nitrophenyloxycarbonylthio)-3S-(1S-(dimethyl-t-butylsilyloxy)ethyl)-2-azetidrnon-1-yl]acetate A solution of 4.06 g (33.2 mmol) of dimethylaminopyridine and 6.69 g (33.2 mmol) of 4-nitrophenylchloroformate was prepared in 700 ml of THF. The solution was cooled to 0° C. and was treated simultaneously with a solution of the entire batch of title product from the preceding Example in 60 ml of THF, and a separate solution of 5.78 ml (33.2 mmol) of diisopropylethylamine in 60 ml of THF. The addition required 0.5 hours and formed a white precipitate. After stirring the mixture for 5 minutes, the reaction mixture was filtered with exclusion of atmospheric moisture and the filtered solution of present title product placed in a constant addition funnel and immediately used in the next step.

A portion of this solution, following filtration through a small portion of silica gel using $CDCl_3$ as eluant was characterized by means of $^1H$-NMR (300 MHz) which showed delta: 8.22 (2H, d, J=8 Hz), 7.29 (2H, d, J=8 Hz), 5.74–5.89 (1H, ddd, J=18 Hz, 12 Hz, J=6 Hz), 5.46 (1H, d, J=2 Hz), 5.25 (1H, d, J=18 Hz), 5.17 (1H, d, J=12 Hz), 4.57 (2H, d, J=6 Hz), 4.25 (1H, dq, J=6 Hz, J=5 Hz), 4.10 (1H, d, J=19 Hz), 3.90 (1H, d, J=19 Hz), 3.27 (1H, dd, J=5 Hz, J=2 Hz), 1.26 (3H, d, J=6 Hz), 0.84 (9H, s), 0.06 (3H, s), 0.04 (3H, s).

EXAMPLE 3

Allyl 5R,6S-2-Oxo-6-[1R-(dimethyl-t-butyl silyloxy)ethyl]penam-3-carboxylate

The entire solution of the product of the preceding Example was added to 133 ml (133 mmol) of 1.0M lithium hexamethyldisilylamide (in THF) which was previously diluted with 1000 ml of THF and cooled to −78° C. The addition required 0.5 hours and the solution turned bright yellow. Acetic acid (38 ml, 664 mmol) was added and the reaction mixture was stirred for 10 minutes. Approximately ½ of the solvent was removed through concentration and the remainder was diluted with diethyl ether to a volume of 2.7 liters. The ether solution was washed with saturated bicarbonate solution, saturated brine solution and then dried over sodium sulfate. The organic phase was concentrated and the residue was filtered through a pad of silica gel eluting with 15% ethyl acetate in hexane. There was obtained 6.98 g (56%) present title product as a waxy solid; m.p. 45°–48° C.; $^1H$-NMR(CDCl$_3$, 300 MHz)delta: 5.78–5.94 (1H, ddd, J=18 Hz, J=11 Hz, J=7 Hz), 5.51 (1H, d, J=2 Hz), 5.32 (1H, d, J=18 Hz), 5.25 (1H, d, J=11 Hz), 5.00 (1H, s), 4.65 (2H, d, J=7 Hz), 4.32 (1H, dt, J=7 Hz, J=4 Hz), 3.54 (1H, dd, J=4 Hz, J=2 Hz), 1.28 (3H, d, J=7 Hz), 0.86 (9H, s), 0.07 (3H, s), 0.05 (3H, s); $C^{13}$—NMR(CDCl$_3$, 75.43 MHz)delta: 199.0, 169.0, 163.4, 130.4, 119.6, 71.7, 67.1, 66.1, 64.6, 62.4, 25.6, 22.5, 17.9, −4.2, −5.1; m/e calculated for $C_{13}H_{18}NO_5SSi[P-tBu]$: 328.0675, found: 328.0615.

EXAMPLE 4

Allyl 5R,6S-6-[1R-(Dimethyl-t-butylsilyloxy)ethyl]-2-(trifluoromethanesulfonyloxy)penem-3-carboxylate A solution of 100 mg (0.260 mmol) of title product of the preceding Example in 5 ml of methylene chloride was treated with 0.180 ml (1.03 mmol) diisopropylethyl amine. This clear solution was then cooled to −78° C. in a dry ice-acetone bath. Freshly distilled triflic anhydride (0.045 ml, 0.270 mmol) was added and the clear solution was stirred for 1 hour at −78° C. to form a cold solution of present title product, which was used directly in the next step.

A small portion of this solution was purified by chromatography on silica gel followed by low temperature (−78° C.) crystallization from pentane; m.p. 40° C.; $^1H$-NMR(CDCl$_3$, 300 MHz)delta: 5.84–5.98 (1H, ddd, J=18 Hz, J=12 Hz, J=6 Hz), 5.73 (1H, d, J=2 Hz), 5.37 (1H, dd, J=18 Hz, J=1 Hz), 5.25 (1H, dd, J=12 Hz, J=1 Hz), 4.73 (2H, dd, J=6 Hz, J-1 Hz), 4.25 (1H, dq, J=6 Hz, J=4 Hz), 3.86 (1H, dd, J=4 Hz, J=2 Hz), 1.24 (3H, d, J=6 Hz), 0.87 (9H, s), 0.08 (6H, s); m/e calculated for $C_{14}H_{17}NO_7S_2SiF_3$[p−tBu]460,0168, found: 460.0246.

EXAMPLE 5

Allyl 5R,6S-6-[1R-(Dimethyl-t-butylsilyloxy)ethyl]-2-[(1R-oxo-3S-thiolanyl)thio]penem-3-carboxylate A solution of 69 mg (0.388 mmol) of 3S-(acetylthio)-thiolane-1R-oxide in 5 ml of methylene chloride was treated with 5 ml of water and was cooled to 0° C. The stirred mixture was charged with 0.78 ml (1.56 mmol) of 2.0M sodium hydroxide and was allowed to stand for 0.5 hours. The reaction mixture was quenched with 0.089 ml (1.56 mmol) acetic acid and was extracted with 5×10 ml of methylene chloride. The organic phase was dried with sodium sulfate, filtered and was then treated with 0.135 ml (0.780 mmol) of diisopropylethyl amine. This solution of 3S-mercaptthiolane-1R-oxide was allowed to stand while the operation of the preceding Example was completed. It was then added to the entire cold solution of the preceding Example over 0.5 hour while maintaining the temperature below −65° C. at all times. After 18 hours at −78° C. the reaction mixture was treated with 10 ml of water and was allowed to warm to room temperature. The product was extracted with methylene chloride and the organic phase was washed with brine and then dried and evaporated. After filtration through silica gel, there was obtained 129 mg (98%) of present title product; m.p. 131°-134° C.; $^1$—NMR(CDCl$_3$, 300 MHz)delta: 5.80–5.96 (1H, ddd, J=18 Hz, J=12 Hz, J=6 Hz), 5.62 (1H, d, J=2 Hz), 5.35 (1H, dq, J=18 Hz, J=2 Hz), 5.19 (1H, dq, J=12 Hz, J=2 Hz), 4.66 (2H, m), 4.21 (1H, dq, J=7 Hz, J=3 Hz), 3.93 (1H, dd, J=14, J=7 Hz), 3.67 (1H, dd, J=3, J=2 Hz), 3.56–3.72 (1H, m), 3.09 (1H, m), 2.54–2.84 (4H, m), 1.23 (3H, d, J=7 Hz), 0.85 (9H, s), 0.05 (6H, s); $C^{13}$—NMR(CDCl$_3$, 75.43 MHz)delta: 171.9, 159.4, 150.8, 131.7, 118.7, 118.5, 71.8, 65.7, 65.2, 64.1, 61.7, 52.7, 46.7, 33.2, 25.7, 22.5, 17.9; m/e calculated for $C_{17}H_{24}NO_5S_3Si$[P−tBu]: 446.0587, found: 446.0597.

EXAMPLE 6

Allyl 5R,6S-6-(1R-Hydroxyethyl)-2-[(1R-oxo-3S-thiolanyl)-thio]penem-3-carboxylate A solution of 100 mg (0.198 mmol) of the title product of the preceding Example in 2 ml of dry THF and 0.114 ml of acetic acid was treated with 0.594 ml (0.594 mmol) 1M tetrabutylammonium fluoride and the solution was allowed to stir at room temperature for 18 hours. The reaction mixture was poured into a mixture of 50 ml ethyl acetate and 10 ml of water. The solution pH was adjusted to 6.4 by the addition of 20% potassium acetate in water. The organic phase was removed and the aqueous layer was washed twice more with 20 ml of ethyl acetate. The combined organic layers were dried over sodium sulfate and then evaporated. The residue was chromatographed on silica gel (32–63 microns) with 15% methanol in ethyl acetate. There was obtained 70.6 mg (92%) of present title product as a solid; m.p. 151°–155° C.; $^1$—NMR(DMSO-d-6, 300 MHz)delta: 596 (1H, m), 5.82 (1H, d, J=3 Hz), 5.45 (1H, dd, J=18 Hz, J=3 Hz), 5.31 (1H, s), 5.29 (1H, dd, J=12 Hz, J=3 Hz), 5.78 (1H, dd, J=18 Hz, J=6 Hz), 5.65 (1H, dd, J=18 Hz, J=6 Hz), 3.77–4.12 (4H, m), 3.08 (1H, m), 2.67–2.98 (3H, m), 2.49 (1H, m), 1.23 (3H, d, J=7 Hz); $C^{13}$-NMR(DMSO-d-6, 75.43 MHz)delta: 173.5, 158.9, 153.6, 132.4, 117.6, 116.2, 71.3, 71.2, 64.6, 63.8, 60.4, 52.2, 46.3, 33.4, 21.4.

EXAMPLE 7

Sodium 5R,6S-6-(1R-Hydroxyethyl)-2-[(1R-oxo-3S-thiolanyl)thio]penem-3-carboxylate A solution of the title product of the preceding Example (30 mg, 0.077 mmol) in 1 ml of methylene chloride was treated with 0.058 ml (0.081 mmol) of sodium ethylhexanoate in ethyl acetate solution (1.39 mmol/ml). The reaction mixture was treated with 6 mg (0.0223 mmol) triphenylphosphine and 6 mg (0.005 mmol) tetrakis(triphenylphosphine) palladium in 0.5 ml of methylene chloride. The mixture was allowed to stir for 1 hour at room temperature. Ethyl acetate (30 ml) was added and the mixture filtered to yield crude product. The latter was taken up in distilled water and treated with a small amount of activated carbon, filtered and the filtrate lyophilized to yield present title product, 10.5 mg; $^1$H-NMR(DMSO-d-6, 300 MHz)delta: 5.52 (1H, d, J=3 Hz), 5.24 (1H, brs), 3.74–3.96 (2H, m), 3.50–3.66 (2H, m), 2.88–2.98 (1H, m), 2.70–2.86 (1H, m), 2.44–2.60 (2H, obscured), 2.2–2.36 (1H, m), 1.14 (3H, d, J=7 Hz).

EXAMPLE 8

Allyl 5R,6S-6-[1R-(Dimethyl-t-butylsilyloxy)ethyl]-2-[(1,1-dioxo-3R- and 3S-thiolanyl)thio]penem-3-carboxylate A solution of 50 mg (0.129 mmol) of the title product of Example 3 at 0° C. in 4 ml of methylene chloride was treated with 0.089 ml (0.51 mmol) diisopropylethyl amine. This clear solution was then cooled to −78° C. in a dry ice-acetone bath. Freshly distilled trifluoromethanesulfonic anhydride (0.024 ml, 0.142 mmol) was added and the clear solution that resulted was stirred for 1 hour at −78° C. The resulting cold solution of Example 4 title product was treated with a solution of 19.6 mg (0.129 mmol) of racemic 3-mercaptothiolane-1,1-dioxide (Bezmenova et al., *Khim. Geterotsikl. Soedin.* 1975, 188, 2; Chem. Abstr. 1975, 170558) and 0.022 ml (0.129 mmol) diisopropylethyl amine in 1 ml of methylene chloride. Addition required 0.5 minutes and the solution temperature was kept below −b 70° C. at all times. After 2 hours at −78° C. the reaction mixture was allowed to warm to room temperature and was stirred overnight. The solution was then treated with 10 ml of water and was extracted with ethyl acetate. The organic phase was washed with brine and then dried and evaporated. After filtration through silica gel (3:2 hexane:ethyl acetate), there was obtained 66.7 mg (100%) present title product as a mixture of diastereomers. These diastereomers were separated by chromatography on silica gel by eluting with a solution of 6:3:1 hexane:ethyl acetate:benzene. The more polar diastereomer had the following properties: m.p. 180°–181° C., [alpha]$_D$=+57.14°(c=0.49 g/100 ml); HRMS calculated for $C_{17}H_{24}NO_6S_3Si$: 462.0536 (P-tBu), found: 462.0473. The less polar diastereomer had the following properties: m.p. 169°–170° C. [alpha]$_D$=+111.78° (c=0.73 g/100 ml); HRMS calculated for $C_{17}H_{24}NO_6S_3Si$: 462.0536 (P-tBu), found: 462.0506.

The blocking groups are removed from these compounds according to the methods of Examples 6 and 7 to yield the known products of Hamanaka, U.S. Pat. No. 4,619,924.

EXAMPLE 9

Allyl 5R,6S-6-[1R-(Dimethyl-t-butylsilyloxy)ethyl]-2-(ethylthio)penem-3-carboxylate Title product of Example 3 (100 mg, 0.262 mmol) was converted to a cold solution of title product of Example 4 according to the method of Example 4. This solution, at −78° C., was treated with a solution of 0.096 ml (1.3 mmol) ethanethiol and 0.226 ml (1.3 mmol) diisopropylethylamine in 1 ml of acetonitrile. Addition required 0.5 minutes and the solution temperature was kept below −70° C. during this time. After 5 minutes at −78° C. the reaction mixture was allowed to warm to 0° C. and was stirred for 2 hours. The solution was then treated with 10 ml of water and was extracted with ethyl acetate. The organic phase was washed with brine and then dried and evaporated. After filtration through silica gel (4:1 hexane:ethyl acetate) there was obtained 110 mg of present title product; m.p. 83°–84° C.; HRMS calculated for $C_{19}H_{31}NO_4S_2Si$: 429.1464, found: 429.1026; a compound earlier reported in racemic form by Leanza et al. Tetrahedron, vol. 39, 2505–2513 (1983).

Present title compound is deblocked according to Examples 6 and 7 to form the corresponding known penem antibiotic previously reported by Gangaly et al., *J. Antimicrobiol. Chemotherapy,* vol. 9, pp. C1–C5 (1982).

EXAMPLE 10

Allyl 5R,6S-6-[1R-(Dimethyl-t-butylsilyloxy)ethyl]-2-(isopropylthio)penem-3-carboxylate By the methods of the preceding Example, title product of Example 3 (105.3 mg, 0.274 mmol) and isopropyl mercaptan (0.239 ml, 1.37 mmol) were converted to present title product, purified by chromatography on silica gel using 19:1 hexane:ethyl acetate as eluant, 60 mg, m.p. 104°–106° C.; previously known in racemic form, Leanza et al., loc. cit.; deblocked by the methods of Examples 6 and 7 to yield the corresponding, known penem antibiotic, Ganguly et al., loc. cit.

EXAMPLE 11

Allyl 5R,6S-6-[1R-(Dimethyl-t-butylsilyloxy)ethyl-2-[(hydroxyethyl)thio]penem-3-carboxylate By the methods of Example 8, the title product of Example 3 (61 mg, 0.158 mmol) and 2-mercaptoethanol (0.012 ml, 0.174 mmol) were converted to present title product, purified by chromatography on silica gel using 3:2 hexane:ethyl acetate as eluant, 60 mg; m.p. 80° C.; [alpha]$_D$= +160.4° (c=2.22 g/100 ml); HRMS calculated for $C_{19}H_{31}NO_5S_2Si$: 445.1412, found: 445.1420.

EXAMPLE 12

Allyl 5R,6S-6-[1R-(Dimethyl-t-butylsilyloxy)ethyl]-2-[2-(4-nitrobenzyloxycarbonylamino)ethylthio]penem-3-carboxylate By the methods of the preceding Example, the title product of Example 3 (49.5 mg, 0.129 mmol) and 2-[(4-nitrobenzyloxycarbonyl)amino]ethyl mercaptan (33 mg, 0.129 mmol; Shinkai et al., Synthesis 1980, 924) were converted to present, chromatographed title product, 71 mg; m.p. 103°–105° C.; [alpha]$_D$= +88.34° (c=3.26 g/100 ml); HRMS calculated for $C_{23}H_{28}N_3O_8S_2Si$: 566.1088 (P-tBu), found: 566.1119.

EXAMPLE 13

Allyl 5R,6S-6-[1R-(Dimethyl-t-butylsilyloxy)ethyl]-2-[1-(4-nitrobenzyloxycarbonyl)-3S-pyrrolidinylthio]penem-3-carboxylate By the methods of Example 8, the title product of Example 3 (101.7 mg, 0.264 mmol) and 3S-mercapto-1-(p-nitrobenzyloxycarbonyl) pyrrolidine (0.050 ml 0.289 mmol; Sigimura et al., Heterocycles 24,1331, 1986) were converted to present title product which, following extraction into ethyl acetate, was purified by chromatography on silica gel using 2:1 hexane:ethyl acetate as eluant, 147 mg; m.p. 105°–106° C.; [alpha]$_D$= +260° (c=0.84, $CHCl_3$).

EXAMPLE 14

2-(Trimethylsilyl)ethyl 5R,6S-2-Oxo-6-[1R-(Dimethyl-t-butylsilyloxy)ethyl]-penem-3-carboxylate By the methods of Examples 1–3 above, 2-(trimethylsilylethyl 2-[4R-(triphenylmethylthio)-3S-(1S-(dimethyl-t-butylsilyloxy)ethyl)-2-azetidinon-1-yl]acetate was converted to present title product; $^1$H-NMR($CDCl_3$, 300 MHz)delta: 5.52 (1H, d, J=3 Hz), 4.96 (1H, s), 4.35 (1H, q, J=8 Hz, J=5 Hz), 4.26 (2H, dt, J=12 Hz), 3.56 (1H, dd, J=5 Hz, J=3 Hz), 1.30 (3H, d, J=8 Hz), 1.06 (2H, dt, J=12 Hz), 0.89 (9H, s), 0.1 (3H, s), 0.08 (3H, s), 0.05 (9H, s); $C^3$ 13-NMR (CDCl, 62.89 MHz)delta: 199.3, 169.2, 163.9, 71.8, 66.4, 65.5, 64.7, 62.5, 25.7, 22.5, 17.9, 17.4, −1.5, −4.2, −5.1; m/e calculated for $C_{15}H_{26}NO_5SSi_2$ [P-t-Bu]388.1179, found: 388.1125.

According to the sequential steps and methods of Examples 4–6, the product is further converted, via key intermediate 2-(trimethylsilyl)ethyl 5R,6S-6-[1R-(dimethyl-t-butylsilyloxy)ethyl]-2-(trifluoromethanesulfonyloxy)penem-3-carboxylate, to 2-(trimethylsilyl)ethyl 5R,6S-6-[1R-(dimethyl-t-butylsilyloxy)ethyl]-2-[(1R-oxo-3S-thiolanyl)thio]penem-3-carboxylate. The dimethyl-t-butylsilyl and trimethylsilylethyl protecting groups are removed by the action of tetrabutylammonium fluoride in THF at room temperature according to the method described in Example 8, above and Girijavallabhan et al., U.S. Pat. No. 4,443,373.

EXAMPLE 15

Pivaloyloxymethyl 5R,6S-6-(1R-Hydroxyethyl)-2-[(1R-oxo-3S-thiolanyl)-thio]penem-3-carboxylate By the sequential steps and methods of Examples 1–6, pivaloyloxymethyl 2-[4R-(triphenylmethylthio)-3S-(1S-(dimethyl-t-butylsilyloxy)ethyl)-2-azetidinon-1-yl]acetate is converted to present title product. The corresponding 1-(ethoxycarbonyloxy)ethyl ester is prepared in like manner.

PREPRATION 1

(R)-3-Thiolanyl p-Toluenesulfonate (R)-4-(methylthio)1,2-butanediol (1.0 , 7.35 mmol) and p-toluenesulfonyl chloride (3.0 g, 15.8 mmol) were combined in 10 ml of pyridine at 0-5° C., then stirred at room temperature, at which time tlc (3:1 hexane:ethyl acetate) indicated no diol (Rf 0.1), appreciable of th ediol ditosylate (Rf 0.53), some intermediate thiolanium salt (Rf 0.03) and a trace of title product (Rf 0.72). The reaction mixture was then heated at 60° C. for 8 hours, at which time tlc (5:1 hexane:ethyl acetate) indicated an appreciable amount of the desired title product (Rf 0.45 ), only a trace of the ditosylate (Rf 0.22), some probable thiolanium salt (Rf 0.0), and other, generally less polar impurities. The cooled reaction mixture was diluted with an equal volume of water and two volumes of ethyl acetate. The organic layer was separated, washed with saturated NaCl, dired ($MgSO_4$), stripped and the residue chromatographed on silica gel using 10:1 g less polar impurities (stench!) and 0.25 g of present, purified title product; tlc Rf 0.55 (4:1 hexane:ethylacetate); [alpha]$_D$= +15.87 (c=0.6, $CH_3OH$).

PREPARATION 2

3R-(p-Toluenesulfonyloxy)thiolane 1R-Oxide

A solution of 46.30 g (0.179 mol) title product of the preceding Preparation in 600 ml acetone, under nitrogen was cooled to 0° C. In a separate flask 61.73 g (0.100 mol) potassium peroxymonosulfate was stirred in 500 ml distilled water until clear. This was added to the acetone solution at 0° C. and the mixture allowed to warm to room temperature. After 25 minutes 75 ml of 10% (w/v) aqueous sodium sulfite was added, the acetone was evaporated, 300 ml ethyl acetate added and the aqueous layer was extracted with ethyl acetate (3×100 ml). The combined extracts were dried ($MgSO_4$) and concentrated to dryness to yield 48.57 g of crude product. The latter was purified by silica gel chromatography using 10:10:1 ethyl acetate:$CH_2C_{12}$ $CH_3OH$ as eluant to afford purified title product, 34.67 g (71%); [alpha]$_D$= +4.26° (c=3.0, $CHCl_3$).

PREPARATION 3

3S-(Acetylthio)thiolane 1R-Oxide

In a flame-dried flask under nitrogen, 31.67 g (0.1156 mol) title product of the preceding Preparation was dissolved in 300 ml acetone and 19.81 g (0.1734 mol)

potassium thioacetate was added. The mixture was heated at reflux for 3.5 hours and allowed to stir at room temperature overnight. The mixture was filtered, rinsed and washed with 500 ml acetone and the filtrate and washings were evaporated in vacuo to obtain 23.96 g of the desired product as an oil. The oil was purified by flash chromatography on a 120 mm×25 cm silica gel column eluting with 19:1 ethyl acetate:methanol collecting 125 ml fractions. Fractions 42-64 were combined and stripped to yield purified title product as an oil which crystallized on standing, 16.46 g; (80%); m.p. 51°-52° C.; [alpha]$_D$= −83.41° (c=0.86, CHCl$_3$).

Analysis calculated for C$_6$H$_{10}$S$_2$O$_2$: C, 40.4; H, 5.6%. Found: C, 40.15; H, 5.53%.

We claim:

1. A process for the preparation of a compound of the formula

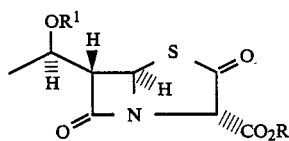
(4)

wherein R is —CH$_2$CX=CH$_2$, —CH$_2$CH$_2$Si(CH$_3$)$_3$, p-nitrobenzyl, or a conventional radical forming an ester which is hydrolyzed under physiological conditions;

X is H or Cl; and

R$^1$ is a conventional silyl protecting group; which comprises (a) reaction of a compound of the formula

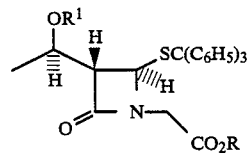
(1)

with a molar excess of AgNO$_3$ in the presence of a molar excess of pyridine in a reaction-inert solvent at a temperature in the range of about −25° to 25° C., followed by treatment with H$_2$S, to form a compound of the formula

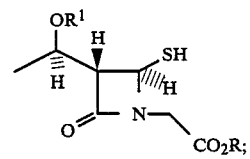
(2)

(b) acylation of said compound of the formula (2) with substantially one molar equivalent of p-nitrophenyl chloroformate in the presence of substantially one molar equivalent of 4-(dimethylamino)pyridine in a reaction-inert solvent at a temperature in the range of about −25° to 25° C. to form a solution of a compound of the formula

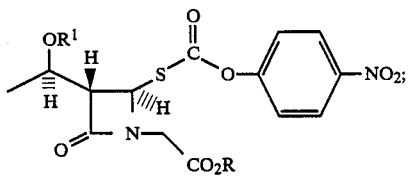
(3)

and (c) reaction of said solution of the compound of the formula (3) with a molar ⓡexcess of lithium hexamethyldisilylamide at a temperature in the range of about −50° to −100° C. to form said compound of the formula (4).

2. A process of claim 1 wherein R$^1$ is dimethyl-t-butylsilyl.

3. A process of claim 1 wherein R is a radial forming an ester group which is —CHR$^2$OCOR$^3$ or —CHR$^2$OCO$_2$R$^3$, where R$^2$ is hydrogen or methyl and R$_3$ is (C$_1$-C$_8$)alkyl.

4. A process of claim 2 wherein R is pivaloyoxymethyl or 1-(ethoxycarbonyloxy)ethyl.

5. A process of claim 2 wherein R is —CH$_2$CH=CH$_2$.

6. A process of claim 2 wherein R is —CH$_2$CH$_2$Si(CH$_3$)$_3$.

7. A process of claim 1 which further comprises conversion of said compound of the formula (4) to a compound of the formula

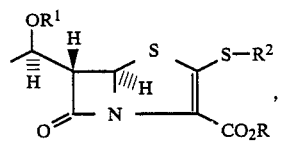
(6)

wherein R and R$^1$ are as defined above and R$^2$ is (C$_1$-C$_4$)alkyl, (1,3-dioxacyclopent-4-yl)methyl, (1,3-dioxacyclopent-2-yl)methyl, (2-oxo-1,3-dioxacyclopent-4-yl)methyl, (1-methyl-2-imidazolyl)methylpiperidinomethyl, 2-hydroxyethyl, 2-(p-nitrobenzyloxycarbonylamino)ethyl, 2-(piperidino)ethyl, 2-(pyrrolidino)ethyl, 2-(morpholino)ethyl, 2-(4-(allyloxycarbonyl)piperazinoethyl, 1-oxo-3-thiolanyl (cis and/or trans), 1,1-dioxo-3-thiolanyl, 1-oxo-3-thianyl (cis and/or trans), 1,1-dioxo-3-thianyl, 1-oxo-4-thianyl (cis and/or trans), 1,i-dioxo-4-thianyl, 4-hydroxy-3-thiolanyl, 4-hydroxy-1-oxo-3-thiolanyl (cis and/or trans), 4-hydroxy-1,1-dioxo-3-thioanyl, 4-hydroxy-3-furyl, 1,3-dioxacyclohex-5-yl, 2-oxo-1,-dioxacyclohex-5-yl, 1-(p-nitrobenzyloxycarbonyl)-3-pyrrolidinyl, 2-oxo-3-pyrrolidinyl, 1-methyl-5-(dimethylaminocarbonyl)-3-pyrrolidinyl, 1-methyl-5-(2-dimethylaminocarbonyl)ethyl-3-pyrrolidinyl, or trans-4-hydroxy-1-(benzyloxycarbonyl)-3-pyrrolidinyl, by the further steps of:

(d) reaction of said compound of the formula (4) with substantially one molar equivalent of triflic anhydride in the presence of a substantially molar excess of diisopropylethylamine in a reaction-inert solvent at a temperature in the range of about −40° to −90° C. to form a solution of a compound of the formula

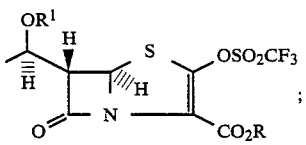 (5)

and (e) reaction of said solution of the compound of the formula (5) with at least one molar equivalent of HS-R$^2$ at a temperature in the range of about 0° to −90° C. to form said compound of the formula (6).

8. A process of claim 7 wherein R$^1$ is dimethyl-t-butylsilyl.

9. A process of claim 7 wherein R is a radical forming an ester group which is —CHR$^2$OCOR$^3$ or —CHR$^2$OCO$_2$R$^3$, where R$^2$ is hydrogen or methyl and R$^3$ is (C$_1$-C$_8$)alkyl.

10. A process of claim 8 wherein R is pivaloyla oxymethyl or 1-(ethoxycarbonyloxy)ethyl.

11. A process of claim 8 wherein R is —CH$_2$CH=CH$_2$.

12. A process of claim 8 wherein R is —CH$_2$CH$_2$Si(CH$_3$)$_3$.

13. A process of claim 11 wherein R$^2$ is

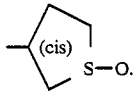

14. A process of claim 11 wherein R$^2$ is

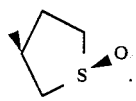

15. A process of claim 11 wherein R$^2$ is

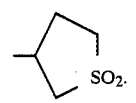

16. A process of claim 11 wherein R$^2$ is —CHCH(CH$_3$)$_2$.

17. A process of claim 11 wherein R$^2$ is —CH$_2$CH$_2$OH.

18. A process for the preparation of a compound of the formula

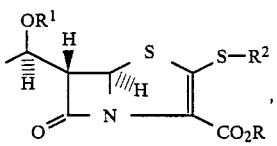 (6)

wherein R is —CH$_2$CX=CH$_2$, —CH$_2$CH$_2$Si(CH$_3$)$_3$, or a conventional radical forming an ester which is hydrolyzed under physiological conditions;

X is H or Cl;

R$^1$ is a conventional silyl protecting group; and

R$^2$ is (C$_1$-C$_4$)-alkyl, (1,3-dioxacyclopent-4-yl)methyl, (1,3-dioxacyclopent-2-yl)-methyl, (1-methyl-(2-oxo-I,3-dioxacyclopent-4-yl)methyl, (1-methyl-2-imidazolyl)methyl, piperidinomethyl, 2-hydroxyethyl, 2-(P-nitrobenzyloxycarbonylamino)ethyl, 2-(piperidino)ethyl, 2-(pyrrolidino)ethyl, 2-(morpholino)ethyl, 2-(4-(allyloxycarbonyl) piperazino-)ethyl, 1-oxo-3-thiolanyl (cis and/or trans), 1,1-dioxo-3-thiolanyl, 1-oxo-3-thianyl (cis and/or trans), 1-dioxo-3-thianyl, 1-oxo-4-thianyl (cis and/or trans), 1,1-dioxo-4-thianyl, 4-hydroxy-3-thiolanyl, 4-hydroxy-1-oxo-3-thiolanyl (cis and/or trans), 4-hydroxy-1,1-dioxo-3-thiolanyl, 4-hydroxy-3-furyl, 1,3-dioxacyclohex-5-yl, 2-oxo-1,3-dioxacyclohex-5-yl, 1-(p-nitrobenzyloxycarbonyl)-3-pyrrolidinyl, 2-oxo-3-pyrrolidinyl, 1-methyl-5-(dimethylaminocarbonyl) -3-pyrrolidinyl, 1-methyl-5-(2-(dimethylaminocarbonyl)-ethyl-3-pyrrolidinyl, or trans-4-hydroxy-1-(benzyloxycarbonyl)3-pyrrolidinyl; which comprises:

(d) reacting a compound of the formula

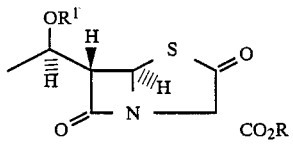 (4)

with substantially one molar equivalent of triflic anhydride in the presence of a substantial molar excess of diisopropylethylamine, in a reaction inert solvent at a temperature in the range of about −40° to −90° C. to form a solution of a compound of the formula

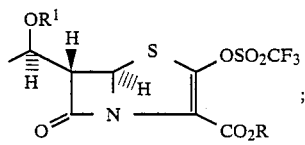 (5)

and (e) reacting said solution of the compound of the formula (5) with at least one molar equivalent of HS—R$^2$ at a temperature in the range of about 0° to −90° C. to form said compound of the formula (6).

19. A process of claim 18 wherein R$^1$ is dimethyl-t-butylsilyl.

20. A process of claim 18 wherein R is a radical forming an ester group which is —CHR$^2$OCOR$^3$ or —CHR$^2$OCO$_2$R$_3$, where R$^2$ is hydrogen or methyl and R$^3$ is (C$_1$-C8)alkyl.

21. A process of claim 19 wherein R is pivaloyloxymethyl or 1-(ethoxycarbonyloxy)ethyl.

22. A process of claim 19 wherein R is —CH$_2$CH=CH$_2$.

23. A process of claim 19 wherein R is —CH$_2$CH$_2$Si(CH$_3$)$_3$.

24. A process of claim 22 wherein R$^2$ is

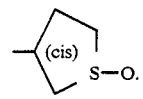

25. A process of claim 22 wherein R$^2$ is

26. A process of claim 22 wherein $R^2$ is
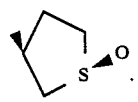
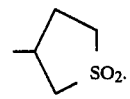
27. A process of claim 22 wherein $R^2$ is —CH$_2$CH(CH$_3$)$_2$.
28. A process of claim 22 wherein $R^2$ is —CH$_2$CH$_2$OH.
* * * * *